(12) United States Patent
Kagermeier et al.

(10) Patent No.: US 7,256,705 B2
(45) Date of Patent: Aug. 14, 2007

(54) TECHNICAL DEVICE AND ASSOCIATED REMOTE CONTROL

(75) Inventors: Robert Kagermeier, Nürnberg (DE); Reiner Staab, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 245 days.

(21) Appl. No.: 10/799,093

(22) Filed: Mar. 12, 2004

(65) Prior Publication Data

US 2005/0017871 A1   Jan. 27, 2005

(30) Foreign Application Priority Data

Mar. 14, 2003  (DE) ................................ 103 11 326

(51) Int. Cl.
*H04Q 1/00* (2006.01)
(52) U.S. Cl. .................................. 340/825.72; 398/106
(58) Field of Classification Search .......... 340/825.72, 340/825.69; 341/176; 398/106; 320/114, 320/115; 5/624
See application file for complete search history.

(56) References Cited

U.S. PATENT DOCUMENTS

| | | | | |
|---|---|---|---|---|
| 4,231,019 A | * | 10/1980 | Junginger et al. | 340/825.76 |
| 4,500,880 A | * | 2/1985 | Gomersall et al. | 340/5.91 |
| 4,728,949 A | * | 3/1988 | Platte et al. | 340/825.37 |
| 4,755,883 A | * | 7/1988 | Uehira | 386/83 |
| 4,872,657 A | * | 10/1989 | Lussi | 5/608 |
| 4,926,456 A | * | 5/1990 | Bock et al. | 378/177 |
| 5,544,376 A | * | 8/1996 | Fromson | 5/618 |
| 5,561,699 A | | 10/1996 | Fenner | |
| 5,900,715 A | * | 5/1999 | Roberts | 320/115 |
| 6,074,388 A | * | 6/2000 | Tockweiler et al. | 606/34 |
| 6,611,979 B2 | * | 9/2003 | Welling et al. | 5/624 |
| 7,079,022 B2 | * | 7/2006 | Kagermeier et al. | 340/514 |

FOREIGN PATENT DOCUMENTS

| | | |
|---|---|---|
| DE | 41 08 347 C2 | 9/1992 |
| EP | 054 72 80 A1 | 6/1993 |

* cited by examiner

*Primary Examiner*—Edwin C. Holloway, III
(74) *Attorney, Agent, or Firm*—Schiff Hardin LLP

(57) ABSTRACT

A technical device and an associated remote control is provided. The remote control includes a support and a contact. The technical device includes a support rail and a contact rail. The support, the contact, the support rail and the contact rail are adapted to one another and fashioned such that an optical and/or electrical effective connection is automatically produced between the contact and the contact rail via attachment of the remote control to the support rail.

35 Claims, 1 Drawing Sheet

TECHNICAL DEVICE AND ASSOCIATED REMOTE CONTROL

BACKGROUND OF THE INVENTION

1. Field of the Invention

The present invention concerns a technical device and an associated remote control that can be attached to the technical device.

2. Description of the Related Art

Operating controls for technical devices are increasingly realized as remote controls. In the one hand, this provides the advantage that the operating controls or elements are not only directly operable while on the device itself, while on the other hand cables for signal lines can be eliminated by a radio frequency or other wireless remote control. This advantage in particular has an effect in very complex technical devices that comprise a plurality of operating elements (such as, for example, display devices or controls) and must correspondingly be cabled in an elaborate and complex manner.

However, a problem of remote controls is that their energy supply cannot ensue over the same wireless connections as the signal transmission. The wireless transmission of energy cannot be used practically over comparably large distances. It is therefore typical to provide remote controls with batteries in order to have an independent voltage supply available. In view of the environmental impact and practical handling of one-time use batteries, rechargeable batteries are frequently used.

Rechargeable batteries wear out at points in time that are not precisely foreseeable, and must therefore be regularly charged. For this reason, a suitable electrical connection to a voltage supply must be provided, whereas the batteries can for the most part still be used in the remote control. For example, the remote control can therefore be plugged into a charging station.

The plug-in location at the charging station allows no flexibility with regard to the place at which the remote control must be located for charging. Moreover, the plug-in space is frequently positioned such that the remote control cannot be reached, or can only be reached in some of the possible use situations. In entertainment electronics, for example, such a plug-in space is frequently on the electronic device itself. In technical devices, the plug-in space can, for example, be located in the region of a control console, and cannot be reached at other workstations that can be spread around the technical device. The same is true for laboratory-technical and medical-technical devices.

SUMMARY OF THE INVENTION

An object of the present invention is to provide a technical device as well as an associated remote control that is flexible with regard to location and at positions that are not spatially predetermined while enabling the creation of an electrical connection of the remote control to an electrical signal source (for example to a voltage supply).

The invention achieves this and other objects via a remote control as well as via a technical device in which the remote control has a support and a contact that is adapted to fit a support rail and a contact rail of the technical device. The support and the contact are provided with an optical and/or electrical effective connection between the contact and the contact rail that is automatically produced upon attachment of the remote control to the rail.

BRIEF DESCRIPTION OF THE DRAWINGS

Exemplary embodiments of the invention are subsequently explained in detail in the Figures.

DESCRIPTION OF THE PREFERRED EMBODIMENTS

Figure 1:
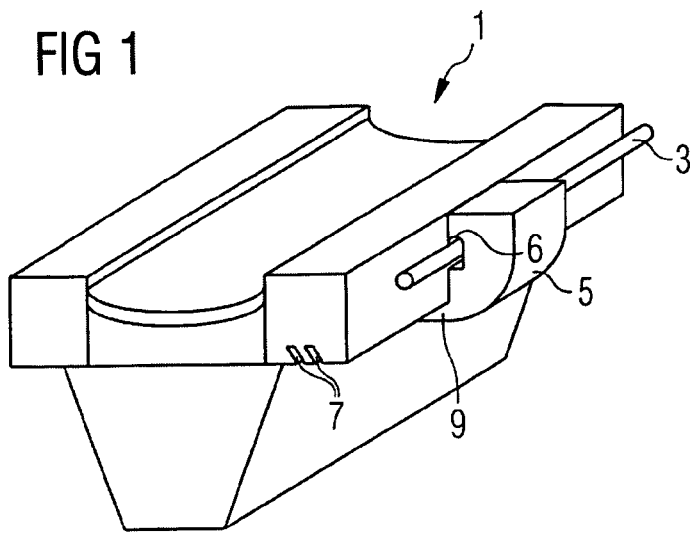
FIG. 1 is an end perspective view of a patient positioning table and remote control with a contact means according to the invention.

A fundamental idea of the invention is to provide a remote control with a support means, adapted to a support rail of a technical device, that comprises a contact means adapted to a contact rail of the technical device such that an effective connection can be automatically produced between the contact means and the contact rail via attachment of the remote control to the support rail. A further fundamental idea of the invention is to provide a technical device with a support rail, adapted to a support means of the remote control, that comprises a contact rail adapted to a contact means of a remote control such that an effective connection can be automatically produced between the contact means and the contact rail via attachment of the remote control to the support rail.

The support rail enables the attachment of the remote control at an arbitrary position over the entire rail length. Likewise, the contact rail can also be contacted by the contact means of the remote control over the entire rail length in order to be able to produce the effective connection between the remote control and the technical device in a way that is flexible with regard to location. The technical device can be a device that is exclusively for attachment of the remote control, however it can also be a device that is controllable and monitorable by the remote control. By effective connection, what should be understood is an electrically active connection that is suitable for transmission of electrical signals, for example a supply voltage. The contact rail and the contact means can be realized simply and allow a short-range electrical connection to be produced via which the electrical signals can be transmitted without a cable or wire connection. Moreover, the effective connection can also be automatically produced via the automatic establishment of the connection upon attachment of the remote control, and no additional controls are required to establish the connection and the operating personnel cannot forget to operate a control to establish the connection. The connection is thus not only flexible with regard to location, but is also automatically produced.

In an advantageous embodiment of the invention, the effective connection comprises an electrically conductive contact. An electrically conductive contact can be simply and reliably produced, for example as a galvanic contact, via the mutual contact of conductive contact surfaces, for example made of metal. The realization of the contact surfaces on the contact rail and the contact means requires only minor expenditure, and electrical contacts are best suitable for transmission of supply voltages.

In a further advantageous embodiment of the invention, the effective connection comprises an inductive connection. Inductive connections enable at short ranges the contact-less transmission of electrical signals in sufficient strength in order to be able to also transmit a supply voltage. An inductive connection is thereby not reliant upon the direct mutual contact of the contact means and the contact rail, and therefore is not susceptible to possible contaminations of the contact surfaces on both sides. Moreover, an inductive signal also represents no personal health or injury danger for people that come in contact with the contact means, which is for example prevalent from induction cooking stoves. Inductive effective connections can, for example, be realized simply using induction coils.

In FIG. 1, a patient positioning table 1 as it is used, for example, in medical diagnostics or therapy is shown as an example of a technical device. However, the technical device could, for example, also be a diagnostic or a therapeutic device, an industrial production device, a building crane such as an assembly crane or an erecting crane or other remotely controllable technical devices. Moreover, the technical device could also be provided for exclusive control by the remote control 5, or the remote control may serve for the control and monitoring of a further different technical devices.

Patient positioning tables can comprise extensive possibilities to change the position of the patient lying thereupon. For example, the height of the table can be automatically changed, and it can be automatically moved forwards or backwards. The table may be used to position the patient in a suitable manner in a further device (not shown) such as, for example, an x-ray device or an MR device. To change the position of the patient positioning table 1 and, as the case may be, also to control and monitor a medical-technical device provided nearby, monitoring elements are necessary that optimally should be arranged in the immediate surroundings of the patient positioning table 1. A patient lying on the patient positioning table 1 can thereby simultaneously be optimally attended, and the medical-technical device can be operated flexibly with regard to location, even though this could, for example, be an x-ray radiation generator arranged in a separate space.

The patient positioning table 1 comprises a support rail 3 to which the operating element can be attached. The support rail 3 extends over a greater part of the length of the patient positioning table 1 in order to be able to attach the operating elements at the position respectively, directly most suitable. In the illustrated preferred embodiment, the support rail 3 is implemented as a type of railing. In further preferred embodiments, it is fashioned as a ridge, as a groove, as a depression or recess on or in the patient positioning table 1, or as a permanent magnet rail.

A remote control 5 is attached to the support rail 3. The remote control 5 comprises a support means 6 adapted to the support rail 3. In the illustrated exemplary embodiment, the support means 6 is formed via a semicircular, oblong depression, open at the bottom, that can engage around the support rail 3 from above and that thereby prevents the remote control 5 from slipping from the support means 6. The remote control 5 is, so to speak, hooked to the support rail 3 via the support means 6. It can be attached at arbitrary longitudinal positions of the support rail 3.

The remote control 5 can, on the one hand, comprise an operating element to change the position of the patient positioning table 1. On the other hand, it can comprise operating elements for medical-technical devices arranged in the surroundings, for example a trigger button for x-ray exposures, as well as display elements that inform about operating parameters of the such devices. The transmission of all signals necessary for this ensues via a wireless connection, for example an infrared or a radio connection that enables the use of the remote control 5 when it is detached from the support rail 3 or, respectively, when it is positioned on the patient positioning table 1. The remote control 5 could thus, for example, also be carried by operating personnel or be attached to the support rail mounted at a different location.

In addition to the wireless, long-range connection for transmission of monitoring signals, a further short-range connection exists between the attached remote control 5 and the patient positioning table 1. This short-range connection is enabled on the part of the patient positioning table 1 via contact rails 7. While two contact rails 7 are provided in the illustrated exemplary embodiment, a single rail or more than two contact rails 7 can also be provided depending on the requirement.

In order to be able to optimally attach the remote control 5 over the entire length of the support rail 3 on the patient positioning table 1, and thereby to be able to automatically produce the effective connection, the contact rails 7 extend over the entire length of the patient positioning table 1 and run parallel to the support rail 3. The remote control 5 can thereby be attached to any arbitrary location on the support rail 3, and simultaneously the effective connection with the patient positioning table 1 can be produced.

To attach the remote control 5, it is placed on the support rail 3 from above and affixed there via the support means 6. It can be rotated in a defined angular range due to the round or, respectively, half-round shape of the support means 6 and the support rail 3. After the placement on the support rail 3, due to the weight the remote control 5 thereby rotates around the support rail 3 such that its lower section moves to the patient positioning table 1 and the contact mounting 9 is on the contact rail 7 from below. In other words, the remote control 5 hangs on the support rail 3. This movement is used to automatically produce the effective connection upon attachment of the remote control 5.

An effective connection can, for example, be produced for the remote control 5 via the contact rails 7. By effective connection, what should thereby be understood is any connection via which the exchange of signals is possible. In a first preferred exemplary embodiment, the effect connection comprises an electrically conductive contact between the contact rails 7 and the remote control 5. In order to be able to produce this electrical contact, the contact rails 7 comprise contact surfaces made from a conductive material (for example a precious metal) that enable the production, for example, of a galvanic contact. The contact surfaces can extend within the contact rails 7 over their entire length and are preferably arranged countersunk in the rails in order to be protected from contact and contamination. The arrangement of the contact rails 7 on an underside of the patient positioning table 1 forms an additional protection from contamination and from unwanted contact.

In order to be able to produce the electrically conductive contact, the remote control 5 likewise comprises contact surfaces that, with the contact surfaces of the contact rails 7, produce an electrical connection as soon as they mutually contact. The shape and attachment of the contact rails 7 and the corresponding contact surfaces of the remote control 5 are provided such that a mutual contact of the contact surfaces in question is automatically formed upon attachment of the remote control 5 to the support rail 5.

In a second preferred exemplary embodiment, instead of an electrical contact, the effective connection comprises an additionally or alternatively provided inductive connection between the contact rails 7 and the remote control 5. In order to be able to produce an inductive connection, electromagnets are arranged in the contact rails 7 with which a magnetic alternating field can be produced, for example via induction coils. This alternating field permeates the contact rails or, respectively, their nearby surroundings, such that a current can be induced in a corresponding inductive sensor of the remote control 5, which is for example an induction coil. The magnetic alternating field is selected to be weak enough that it causes no noteworthy interference signals in the surroundings of the device, however is strong enough that it is suitable for transmission of signals over the short distance to the induction coils of the remote control 5. For example, an energy that is sufficient as a supply voltage can be transmitted over this short range.

In a third preferred exemplary embodiment, an optical connection is provided as an effective connection, in that light of a suitable wavelength is emitted in the contact rails 7. For this, light conductors that connect with a light source can be arranged in the contact rails 7, or light sources themselves can be provided, for example by LEDs. The emitted light can be received by the remote control 5 and transduced into electrical signals via opto-electronic components, for example photodiodes. The optical connection likewise profits from the short separation between the contact rail 7 and the remote control 5, since more energy can be transmitted and fewer interferences can get in the path of the transmission.

The attachment of the contact rails 7 to an underside of the patient positioning table 1 is also advantageous given an inductive or optical effective connection. On the one hand, interfering influences are emitted by the patient due to the electromagnetic or optical signals from the contact rails, on the other hand an unwanted contact and a contamination of the contact rails 7 is more improbable. Contaminations are in particular to be prevented given an optical effective connection, just as in an electrically conductive contact.

Figure 2:
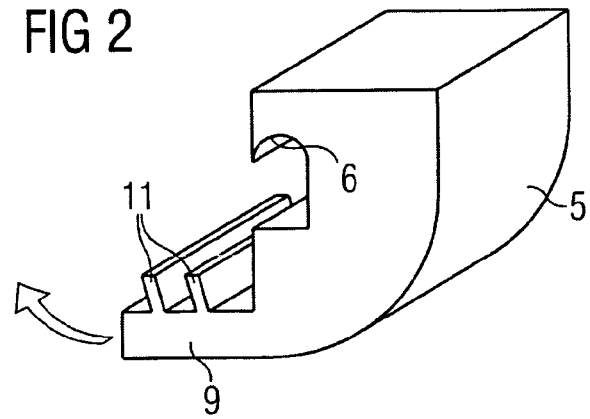
FIG. 2 is a perspective view of a remote control with the contact means according to the invention.

The remote control 5 is shown alone and enlarge in FIG. 2. The arrow in the representation indicates the rotation movement of the remote control 5 (specified above) upon attachment to the support rail 3.

In addition to the support means 6 and the contact mounting 9, it is to be recognized that contact means 11 that serve as a counterpart to the contact rails 7 are arranged on the contact mounting 9. The contact means 11 are formed such that they alone can slide into the contact rails 7 upon attachment of the remote control 5. Their shape and their number is therefore adapted to the shape of the contact rails 7. Moreover, they are angled or offset such that they can slide into the contact rails 7 without resistance as a result of a rotation movement of the remote control 5. In an embodiment (not shown), they can additionally be implemented in a bent configuration in an adaptation to their motion in the rotation movement specified above.

To produce an electrical contact, the contact means 11 comprise contact surfaces that are preferably formed from a precious metal, and that are preferably arranged on the top of the contact means 11. As an alternative to this, the contact means 11 can be completely comprised of a suitable conductive material, for example metal, or one of their lateral flanks can be provided with the metal, preferably the surface that is pressed against the device given the rotation movement specified above.

In an embodiment (not shown), spring mechanisms that, for example, enable the top of the contact means 11 to be flexibly pressed into the contact rail 7 are provided to improve the mutual contact of the contact means 11 with the contact rails 7. For example, height differences between the contact rails 7 or the contact means 11 can thereby be compensated.

To produce an optical effective connection, instead of conductive contact surfaces, the contact means 11 can comprise optical sensors or, respectively, opto-electronic components that are in the position to acquire light from the contact rails 7 and transduce it into electrical signals. To produce an inductive effective connection, the contact means 11 can comprise coils in which an alternating field generated by the contact rails 7 can induce a current.

Figure 3:
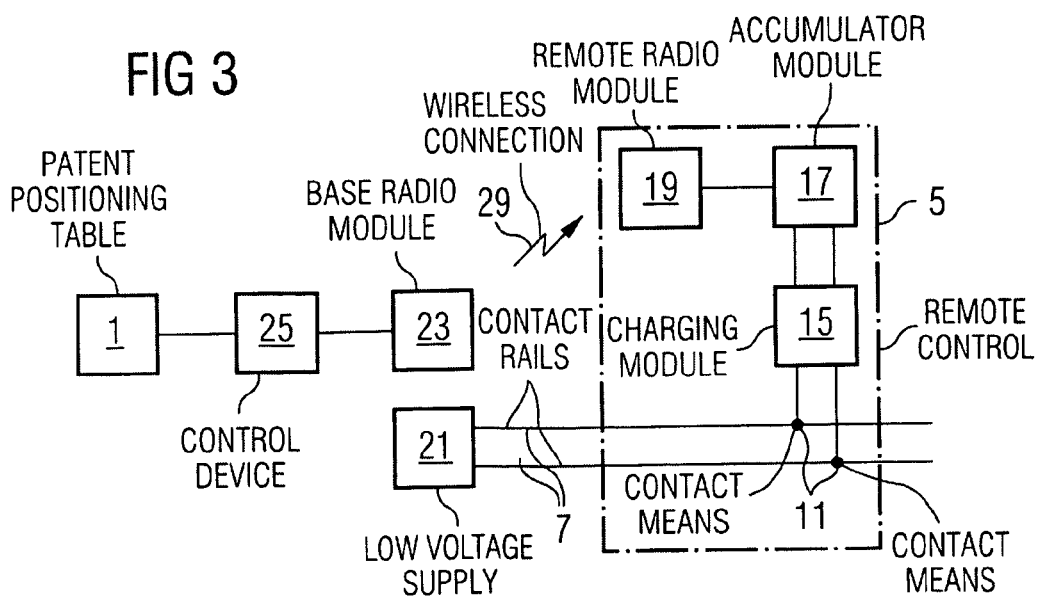
FIG. 3 is a functional block diagram of the electrical function groups for realization of the invention.

In FIG. 3, the electronic components of the remote control 5 as well as on the sides of the patient positioning table 1 are drawn. In addition to the contact means 11, the remote control 5 comprises a charging module 15 that serves to receive a supply voltage via the effective connection. An accumulator module 17 with rechargeable batteries is charged by means of the charging module 15 when the supply voltage is applied.

The accumulator module 17 serves to supply the remote radio module 19 with a supply voltage. Due to this arrangement, it is possible to use the remote control 5 flexibly with regard to location at any time given a charged accumulator module 17, and additionally to always automatically charge the accumulator module 17 when it receives a supply voltage via the contact means 11. It is thereby also possible to charge the remote control 5 at any arbitrary technical device that comprises a suitable support rail 3 and contact rails 7.

On the sides of the patient positioning table 1, a low-voltage supply 21 is provided that is connected with the contact rails 7, and either an electrical potential or an optical signal or a signal to generate a magnetic alternating field is applied to it. Furthermore, a base radio module 23 via which a wireless connection 29 to the remote radio module 19 can be produced is provided on the sides of the patient positioning table 1 or (as the case may be) additional technical devices. The other technical devices may also have a rail via which the same remote control is connected. The base radio module 23 is connected with a control device 25 via which the patient positioning table 1 or (as the case may be) the additional technical device is controlled, for example to change the position of the patient or to trigger an x-ray exposure.

The remote control 5 and the technical device together form a system in which the remote control 5 can be attached to the support rail 3 of the technical device via the support means 6 and the contact means 11 that are adapted to the support rail 3 and the contact rail 7 of the technical device, whereby an optical and/or electrical effective connection is automatically produced between the contact means 11 and the contact rail 7 via attachment of the remote control 5 to the support rail 6.

The transmission of a supply voltage and the transmission of monitoring signals are fundamentally independent of one another, and the corresponding components must not be mutually arranged on the same technical device. In particular, a suitable voltage supply can be provided at many different locations in the work environment or at additional technical devices in order to be able to optimally use and recharge the remote control 5 flexibly with regard to location.

Although other modifications and changes may be suggested by those skilled in the art, it is the intention of the inventors to embody within the patent warranted hereon all changes and modifications as reasonably and properly come within the scope of their contribution to the art.

We claim:

1. A remote control, comprising:
   a support and a contact of the remote control;

a support rail and a contact rail of a technical device, said support and said contact being fashioned such that at least one of an optical and electrical effective connection is automatically produced between said contact and said contact rail via attachment of said remote control to said support rail, said support rail and said contact rail being elongated to permit said remote control to be positioned at a plurality of arbitrary positions along said support rail while providing said at least one of optical and electrical effective connection between said contact rail and said remote control to provide power to said remote control at said plurality of arbitrary positions.

2. A remote control according to claim 1, wherein the effective connection is an electrically conductive contact to carry power from said contact rail to said remote control.

3. A remote control according to claim 1, wherein the effective connection is an inductive connection to carry power from said contact rail to said remote control.

4. A remote control according to claim 1, wherein the effective connection is an optical connection.

5. A remote control according to claim 1, wherein the remote control is supplied with an electrical voltage via the effective connection.

6. A remote control according to claim 5, further comprising:
 a charging module connected with said contact; and
 an accumulator module connected with said charging module.

7. A technical device and a remote control, comprising:
 a support rail and a contact rail of a technical device, said support rail and said contact rail being elongated and extending along a substantial portion of said technical device;
 a support and a contact of said remote control adapted to connect to said support rail and said contact rail, said support being shaped to automatically position said contact of said remote control in effective connection with said contact rail when said remote control is supported on said support rail by said support;
 said support rail and said contact rail being fashioned such that at least one of an optical and electrical effective connection is automatically produced between said contact and said contact rail via attachment of said remote control to said support rail; and
 said remote control being mountable at a plurality of arbitrary locations along said support rail and said contact rail, said remote control being operable to control said technical device when at said arbitrary locations.

8. A technical device according to claim 7, wherein the effective connection is an electrically conductive contact to carry power from said contact rail to said remote control.

9. A technical device according to claim 7, wherein the effective connection is an inductive connection to carry power from said contact rail to said remote control.

10. A technical device according to claim 7, wherein the effective connection is an optical connection.

11. A technical device according to claim 7, wherein an electrical supply voltage is made available via the effective connection to charge a power storage in said remote.

12. A technical device according to claim 11, wherein the contact rail is connected with a low-voltage supply.

13. A technical device according to claim 7, wherein said technical device is a medical-technical device.

14. A technical device according to claim 13, wherein said medical or technical device is a patient positioning table, said support rail and said contact rail extending over a greater part of length of said patient positioning table.

15. A remote control according to claim 1, wherein the support is formed via a semicircular depression that is open at a bottom of the support and can engage part way around the support rail.

16. A remote control according to claim 1, wherein the remote control comprises operating elements that can be used by a user to operate said technical device when said remote control is attached to said support rail and said contact rail.

17. A remote control according to claim 1, wherein said contact is comprised of contact elements that are shaped to slide into effective contact said contact rail upon attachment of the remote control.

18. A remote control according to claim 1, wherein said contact rail is arranged on an underside of said technical device, and said contact is arranged on said remote control so as to extend to said underside of said technical device so as to move into contact with said contact rail when said support is positioned on said support rail.

19. A remote control according to claim 18, wherein said support is disposed relative to said contact so that when said support is engaged on said support rail, said remote is able to rotate to move said contact into engagement with said contact rail from below.

20. A remote control according to claim 1, wherein said technical device is a patient positioning table, and said support rail and said contact rail being separate and spaced from one another, said support rail and said contact rail extending along a greater part of a length of said patient positioning table.

21. A remote control according to claim 1, wherein said support rail is adapted to allow an attachment of the remote control at an arbitrary position along an entire length of the support rail.

22. A remote control according to claim 1, wherein said contact rail is adapted to allow a contact of the remote control at an arbitrary position along an entire length of the contact rail.

23. A technical device and remote control according to claim 7, wherein the support is formed via a semicircular depression that is open at a bottom of the support and can engage part way around the support rail.

24. A technical device and remote control according to claim 7, wherein the remote control comprises operating elements that can be used by a user to control said technical device when said remote control is attached to said support rail and said contact rail.

25. A technical device and remote control according to claim 7, wherein said contact is comprised of contact elements that are shaped to slide into slots in said contact rail upon attachment of the remote control.

26. A technical device and remote control according to claim 7, wherein said contact rail is arranged on an underside of the technical device.

27. A technical device and remote control according to claim 7, wherein said contact is moved on said contact rail from below.

28. A technical device and remote control according to claim 7, wherein the technical device is a patient positioning table and said contact rail and said support rail extent along a substantial length of said patient positioning table.

29. A technical device and remote control according to claim 7, wherein said support rail is adapted to allow an attachment of the remote control at an arbitrary position along an entire length of the support rail.

30. A technical device and remote control according to claim 7, wherein said contact rail is adapted to allow a contact of the remote control at an arbitrary position along an entire length of the contact rail.

31. A remote control as claimed in claim 1, wherein said support rail and said contact rail are separate and spaced apart from one another.

32. A technical device and a remote control as claimed in claim 7, wherein said support is substantially hook shaped, and said contact and said contact rail are disposed relative to said support such as to permit force of gravity to be brought into effective contact between said contact and said contact rail.

33. A technical device and a remote control as claimed in claim 32, wherein said support is shaped to permit rotation of said remote into position with effective contact between said contact and said contact rail.

34. A remote control as claimed in claim 1, wherein said support rail is at least one of: a ridge, a groove, a depression, a recess, and a permanent magnet rail.

35. A remote control as claimed in claim 20, wherein said support rail and said contact rail extend over an entire length of said patient positioning table.

* * * * *